United States Patent
Iranitalab

(10) Patent No.: US 7,751,886 B1
(45) Date of Patent: Jul. 6, 2010

(54) GUIDED ATRIAL ANTI-TACHYCARDIA PACING FOR IMPLANTED CARDIAC STIMULATION

(75) Inventor: Pajhand Iranitalab, San Ramon, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 343 days.

(21) Appl. No.: 11/778,415

(22) Filed: Jul. 16, 2007

(51) Int. Cl.
*A61N 1/00* (2006.01)
(52) U.S. Cl. .......................................................... 607/9
(58) Field of Classification Search ................ 607/9–16
See application file for complete search history.

(56) References Cited

U.S. PATENT DOCUMENTS

| | | | |
|---|---|---|---|
| 5,800,465 | A | 9/1998 | Thompson et al. |
| 6,473,645 | B1 | 10/2002 | Levine |
| 6,477,417 | B1 | 11/2002 | Levine |
| 6,606,516 | B2 | 8/2003 | Levine |
| 2001/0005790 | A1 | 6/2001 | Ripart |
| 2002/0151934 | A1 | 10/2002 | Levine |
| 2002/0151935 | A1 | 10/2002 | Levine |
| 2002/0193834 | A1 | 12/2002 | Levine |
| 2005/0033137 | A1* | 2/2005 | Oral et al. .................... 600/374 |
| 2006/0089637 | A1* | 4/2006 | Werneth et al. ............... 606/41 |

* cited by examiner

*Primary Examiner*—George Manuel
*Assistant Examiner*—Shubatra Narayanaswamy
(74) *Attorney, Agent, or Firm*—Steven M. Mitchell

(57) ABSTRACT

An implantable stimulation device that maps the location of irritable foci causing an atrial arrhythmia is provided by certain embodiments disclosed herein. The device may, for example, collect intra-cardiac data from a plurality of electrodes spatially distributed throughout a chamber of the heart. This data may be compared with data related to the location of each electrode and the electrical properties of the heart to approximate a point of origin for the atrial arrhythmia. Further embodiments may provide methods and systems for using this information to provide more efficient treatment of the atrial arrhythmia. For example, an optimized ATP pulse train may be determined based on the location of one or more irritable foci. Such an ATP pulse train may be applied to more efficiently terminate the atrial arrhythmia.

34 Claims, 7 Drawing Sheets

GUIDED ATRIAL ANTI-TACHYCARDIA PACING FOR IMPLANTED CARDIAC STIMULATION

BACKGROUND OF THE INVENTION

1. Field of the Invention

The present invention generally relates to an implantable cardiac device. The present invention more particularly relates to an implantable device capable of approximating and mapping the location of abnormal electrical signals in the heart and delivering electrical stimulation to the heart based on the source of the abnormal electrical signals.

2. Description of the Related Art

Cardiac arrhythmia is a group of conditions in which the heart beats irregularly or at a rate faster or slower than normal. One such condition is a tachycardia, an abnormally rapid beating of the heart. A resting heart rate above 100 beats per minute in an average adult is typically considered a tachycardia. This increased heart rate may result from dysfunctional electrical activity in the heart. This is often caused when electrical signals generated by one or more irritable foci located in either the atrium or the pulmonary veins replace the regular impulses of the sinoatrial node (SA node). For example, atrial fibrillation is the result of rapid, disorganized electrical impulses usually caused by one or more irritable foci. A related condition, atrial flutter, is characterized by a rapid and regular atrial rate, often near 300 beats per minute. The contraction of the atrium in patients having these conditions is inefficient, resulting in blood stagnation. Thus, atrial fibrillation and atrial flutter create a risk of blood clotting and stroke and significantly reduce the performance of the heart.

One desirable way to treat atrial fibrillation and atrial flutter is to use efficient electrical pacing of the heart. For example, high rate anti-tachycardia pacing (ATP) may override the irritable foci causing the condition and allow the SA node to resume control. ATP may be performed by an implanted device such as a cardioverter-defibrillator or pacemaker. Efficient pacing is desired for several reasons. By treating the condition efficiently, the treatment time may be reduced, lowering the damage and risk to the patient with the condition. Additionally, relatively efficient ATP may reduce patient discomfort caused by strong or unnecessary electrical stimulation.

Systems for pacing the heart of a patient experiencing a condition such as atrial flutter or atrial fibrillation have been developed, but may operate relatively inefficiently. For example, U.S. Pat. No. 5,800,465 titled "System and Method for Multisite Steering of Cardiac Stimuli" describes a system for directing a pulse train towards a target site using a linear lead having multiple electrodes. These systems allow for directed ATP and may attempt to optimize certain pulse characteristics to provide more efficient treatment. However, these systems are essentially linear and not able to locate the source of a condition in the heart, such as the irritable foci causing dysfunctional cardiac activity. Such systems may treat two conditions arising from different locations in essentially the same way, or may not effectively deliver a preferred treatment in a relatively short amount of time. Thus, these systems may result in avoidable lengthening of treatment time, increasing a patient's health risks. Additionally, these systems may provide unnecessary electrical stimulations that result in patient discomfort and further deplete the battery of the implanted device. It will be understood that these devices have limited life span and replacement of batteries requires surgery. The implanted devices of these systems are also not able to provide a physician with information identifying the location of the irritable foci, which may be useful to the physician in diagnosis or in performing other treatments, such as ablation therapy.

Thus, there exists a need for an implanted system that allows for more efficient treatment of atrial fibrillation and flutter. To this end, there is a need for a system that can locate one or more irritable foci responsible for atrial flutter or atrial fibrillation and use this information to develop a more efficient therapeutic response.

SUMMARY OF THE INVENTION

An implantable stimulation device that maps the location of irritable foci causing an atrial arrhythmia is provided by certain embodiments disclosed herein. The device may, for example, collect intra-cardiac data from a plurality of electrodes spatially distributed throughout a chamber of the heart, such as the right atrium. This data may be compared with data related to the location of each electrode and the electrical properties of the heart to approximate an origin for the atrial arrhythmia. Further embodiments may provide methods and systems for using this information to provide more efficient treatment of the atrial arrhythmia. For example, a therapeutic stimulation, such as an ATP pulse train, may be determined based on the location of one or more irritable foci. Such a therapeutic stimulation may be applied to more efficiently terminate the atrial arrhythmia. The more efficient treatment may result in fewer shocks being necessary, which would allow for increased patient comfort while decreasing associated health risks and prolonging battery life.

In one implementation, an implantable cardiac stimulation device is provided. The implanted device comprises at least one lead adapted to be implanted proximate to the atrial walls of the heart and a plurality of electrodes coupled to at least one lead so as to be spatially distributed with respect to the atrial walls of the heart. The device further comprises a controller that receives signals indicative of the electrical activity of the heart from the plurality of electrodes and can induce the delivery of therapeutic stimulation to the heart. The controller detects the existence of a supra-ventricular tachycardia event (SVT) such as based upon the signals received from the plurality of electrodes and uses the signals from the plurality of electrodes to determine location information about the focus of the supra-ventricular tachycardia (SVT).

In another embodiment, an implantable device capable of measuring cardiac activity and providing stimulation to a patient's heart or determining where therapy should be delivered is provided. The implantable device comprises a processor and a housing which contains the processor and the memory, and which is also and configured to be implanted into a patient's body. The device further comprises a plurality of electrodes located external to the housing. Each electrode is capable of transmitting a signal indicative an intrinsic electrical signal originating in the heart to the processor as well as providing an electrical stimulation to the heart. The processor is capable of determining a location or origin of the intrinsic signal electrical stimulation based upon the plurality of signals received by the processor from the plurality of electrodes and storing data representing the location or origin of the intrinsic electrical signal in the memory. The processor is further capable of determining an appropriate therapeutic electrical stimulation based upon the location or origin of the intrinsic electrical signal, and capable of inducing at least one of the plurality of electrodes to deliver electrical stimulation of, preferably millisecond duration, to the heart based upon the determined appropriate therapeutic electrical stimulation.

In yet another implementation, a method for approximating an origin of an intrinsic electrical signal generated in a heart utilizing an implanted device including a plurality of electrodes spatially distributed in a chamber of the atria is provided. The method comprises determining whether an intrinsic electrical signal has been detected by one of the plurality of electrodes and storing data corresponding to a time when the intrinsic electrical signal has been detected when the electrical signal has been detected. These steps of determining whether the intrinsic electrical signal has been detected and storing the set of data are repeated for each of the plurality of electrodes. The times when the intrinsic electrical signal has been detected by each of the plurality of electrodes are used in conjunction with physical location information about each of the plurality of electrodes to approximate the origin of the intrinsic electrical signal.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENT

Figure 1:
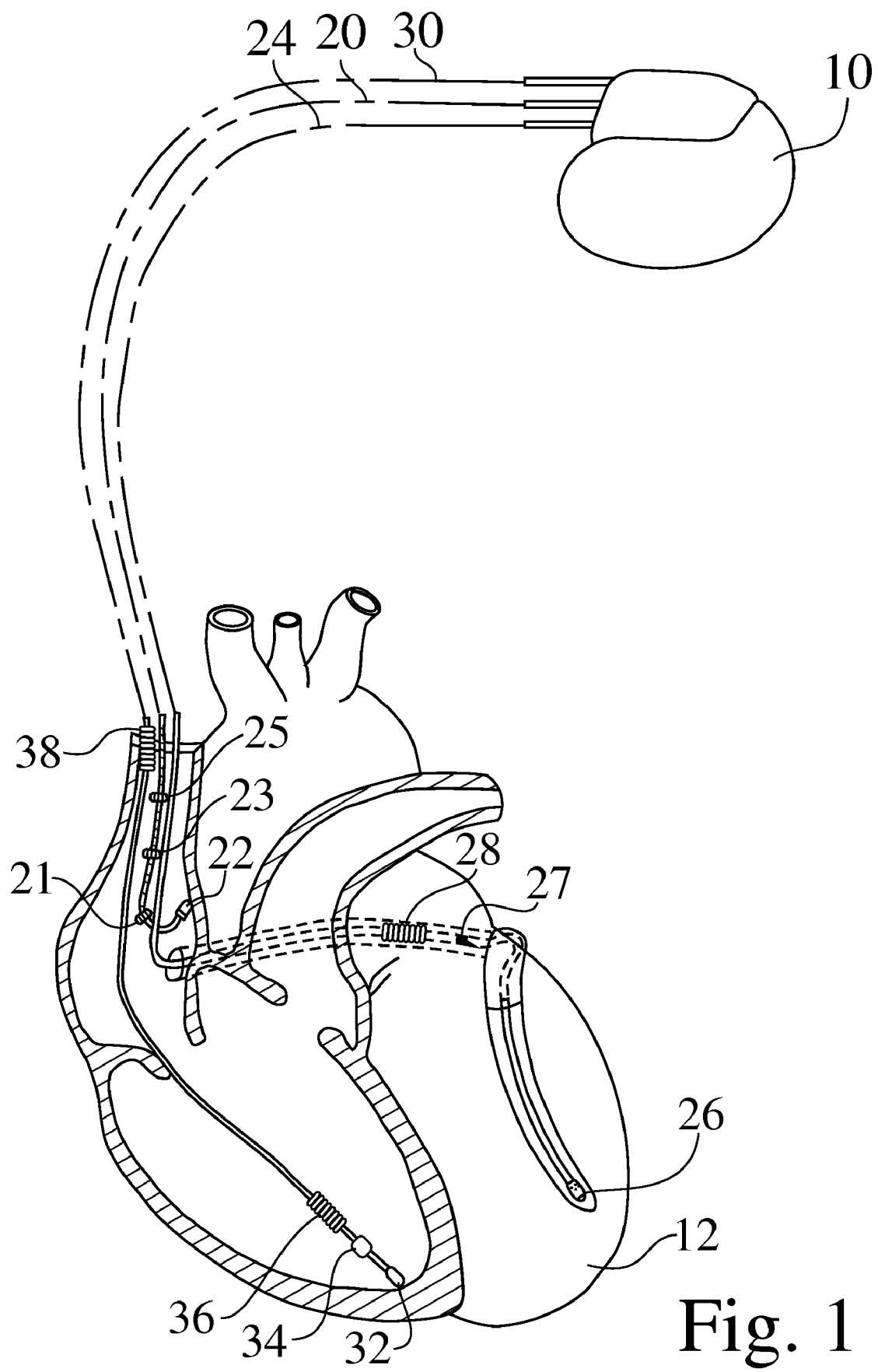
FIG. 1 is a simplified diagram illustrating an implantable stimulation device in electrical communication with at least three leads implanted into a patient's heart for delivering multi-chamber stimulation and shock therapy, according to an embodiment of the invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. In the embodiment shown, right atrial lead 20 additionally has three atrial ring electrodes 21, 23, and 25. As will be described in greater detail below, having multiple electrodes that are spatially distributed through a single chamber of the heart, such as the right atrium, may allow for the approximation of the source of an electrical stimulation, such as the focus of an atrial fibrillation or atrial flutter. In some implementations, the more spatially distributed sensors available in a chamber of the heart, the more accurate this determination may be. Thus, an embodiment is shown in FIG. 1 in which right atrial lead 20 has three atrial ring electrodes 21, 23, and 25, whereas standard right atrial leads commonly have only right atrial tip electrode 22 to sense the electrical activity of the heart.

To sense left atrial and ventricular cardiac signals and to provide left chamber pacing therapy, the stimulation device 10 is coupled to a "coronary sinus" lead 24 designed for placement in the "coronary sinus region" via the coronary sinus is for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/196,898, "A Self-Anchoring Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
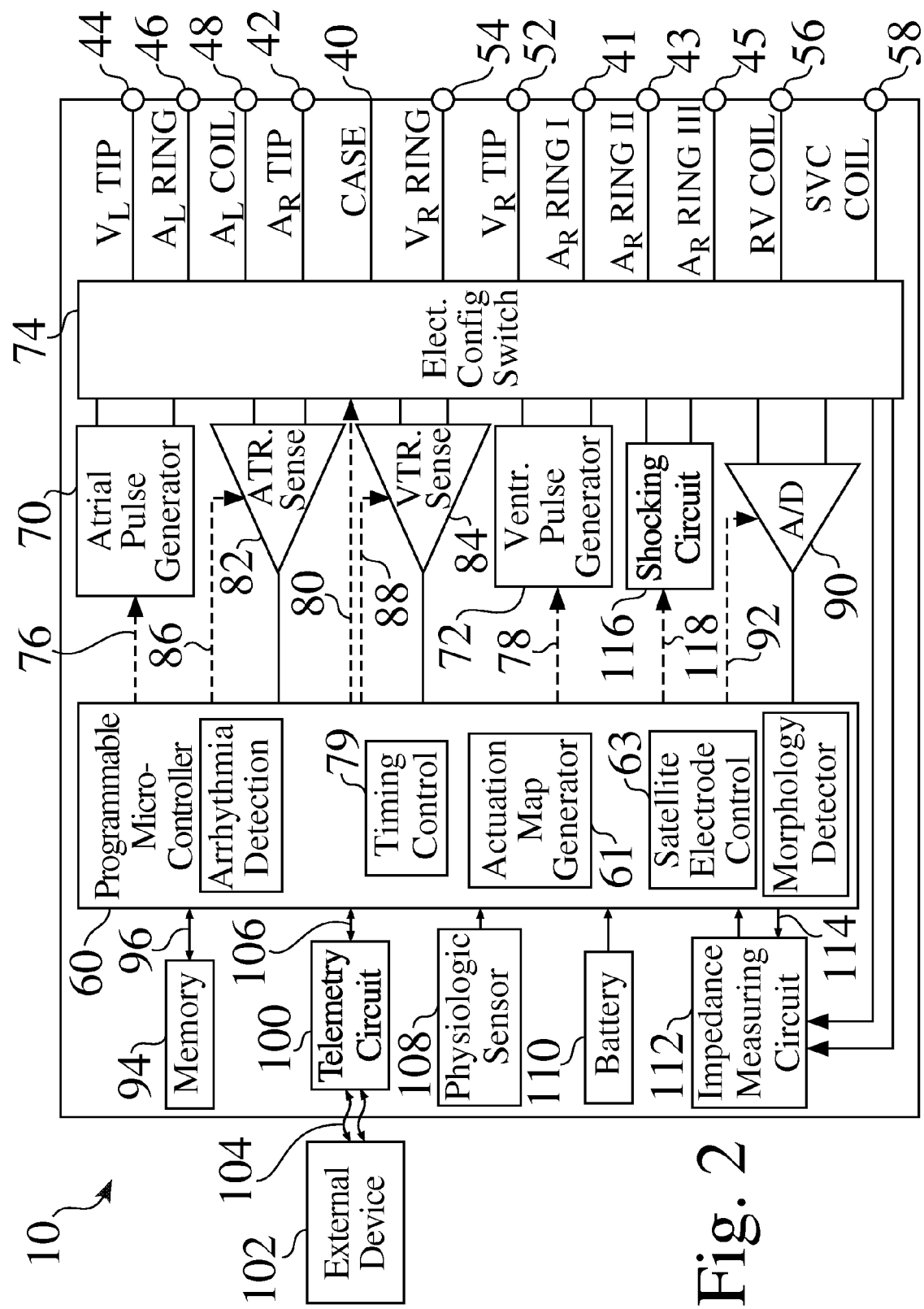
FIG. 2 is a functional block diagram of a multi-chamber implantable stimulation device illustrating the basic elements of a stimulation device, which can provide cardioversion, defibrillation and pacing stimulation in four chambers of the heart capable of communicating with the implanted stimulation device when implanted, according to an embodiment of the invention.

As illustrated in FIG. 2, a simplified block diagram is shown of the multi-chamber implantable stimulation device 10, which is capable of treating both fast and slow arrhythmias with stimulation therapy, such as cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case", or "case electrode" and can be programmably selected to act as the return electrode in some implementations. The housing 40 can further be used as a return electrode alone or in combination with one or more of the coil electrodes, 28, 36 and 38, for shocking purposes. The housing 40 further comprises a connector (not shown) having a plurality of terminals, 41, 42, 43, 44, 45, 46, 48, 52, 54, 56, and 58 (shown schematically and, for convenience, the names of the electrodes to which they are connected are shown next to the terminals). As such, to achieve right atrial sensing and pacing, the connector comprises at least a right atrial tip terminal (AR TIP) 42 adapted for connection to the atrial tip electrode 22. In the embodiment shown, the connector further comprises right atrial ring terminal (AR RING I) 41, right atrial ring terminal (AR RIGHT II) 43, and right atrial ring terminal (AR RING III) 45 adapted for connection to the three atrial ring electrodes 21, 23, and 25, respectively.

To achieve left chamber sensing, pacing and shocking, the connector comprises at least a left ventricular tip terminal (VL TIP) 44, a left atrial ring terminal (AL RING) 46, and a left atrial shocking terminal (AL COIL) 48, which are adapted for connection to the left ventricular tip electrode 26, the left atrial ring electrode 27, and the left atrial coil electrode 28, respectively.

To support right chamber sensing, pacing and shocking, the connector further comprises a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically comprises a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 comprises the ability to process or monitor input signals (data) as controlled by a program code stored in a designated block of memory. The details of the design and operation of the microcontroller 60 are not critical to the present invention. Rather, any suitable microcontroller 60 can be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, can include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further comprises timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 comprises a plurality of switches for connecting the desired electrodes to the appropriate I/O circuits, thereby providing electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 can also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, can include dedicated sense amplifiers, multiplexed amplifiers, or shared amplifiers. The switch 74 determines the "sensing polarity" of the cardiac signal by selectively closing the appropriate switches, as is also known in the art. In this way, the clinician can program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram (EGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection can occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape, and vector of each shocking pulse to be delivered to the patient's heart 12 within each respective tier of therapy. An embodiment of the invention senses and stores a relatively large amount of data (e.g., from the data acquisition system 90), which data can then be used for subsequent analysis to guide the programming of the device 10.

Advantageously, the operating parameters of the implantable device 10 can be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further comprises a physiologic sensor 108, commonly referred to as a "rate-responsive" sensor because it is typically used to adjust pacing stimulation rate according to the exercise state of the patient. However, the physiological sensor 108 can further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 can also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors, which sense the oxygen content of blood, respiration rate and/or minute ventilation, pH of blood, ventricular gradient, etc. However, any sensor can be used which is capable of sensing a physiological parameter which corresponds to the exercise state of the patient. The type of sensor used is not critical and is shown only for completeness.

The stimulation device additionally comprises a battery 110, which provides operating power to the circuits shown in FIG. 2. For the stimulation device 10, which employs shocking therapy, the battery 110 is capable of operating at low current drains for long periods of time, and then be capable of providing high-current pulses (for capacitor charging) when the patient requires a shock pulse. The battery 110 also has a predictable discharge characteristic so that elective replacement time can be detected. Accordingly, the device 10 preferably employs lithium/silver vanadium oxide batteries.

The stimulation device 10 further comprises a magnet detection circuitry (not shown), coupled to the microcontroller 60. It is the purpose of the magnet detection circuitry to detect when a magnet is placed over the stimulation device 10, which magnet can be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having a impedance measuring circuit 112, which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode can be used.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 can act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
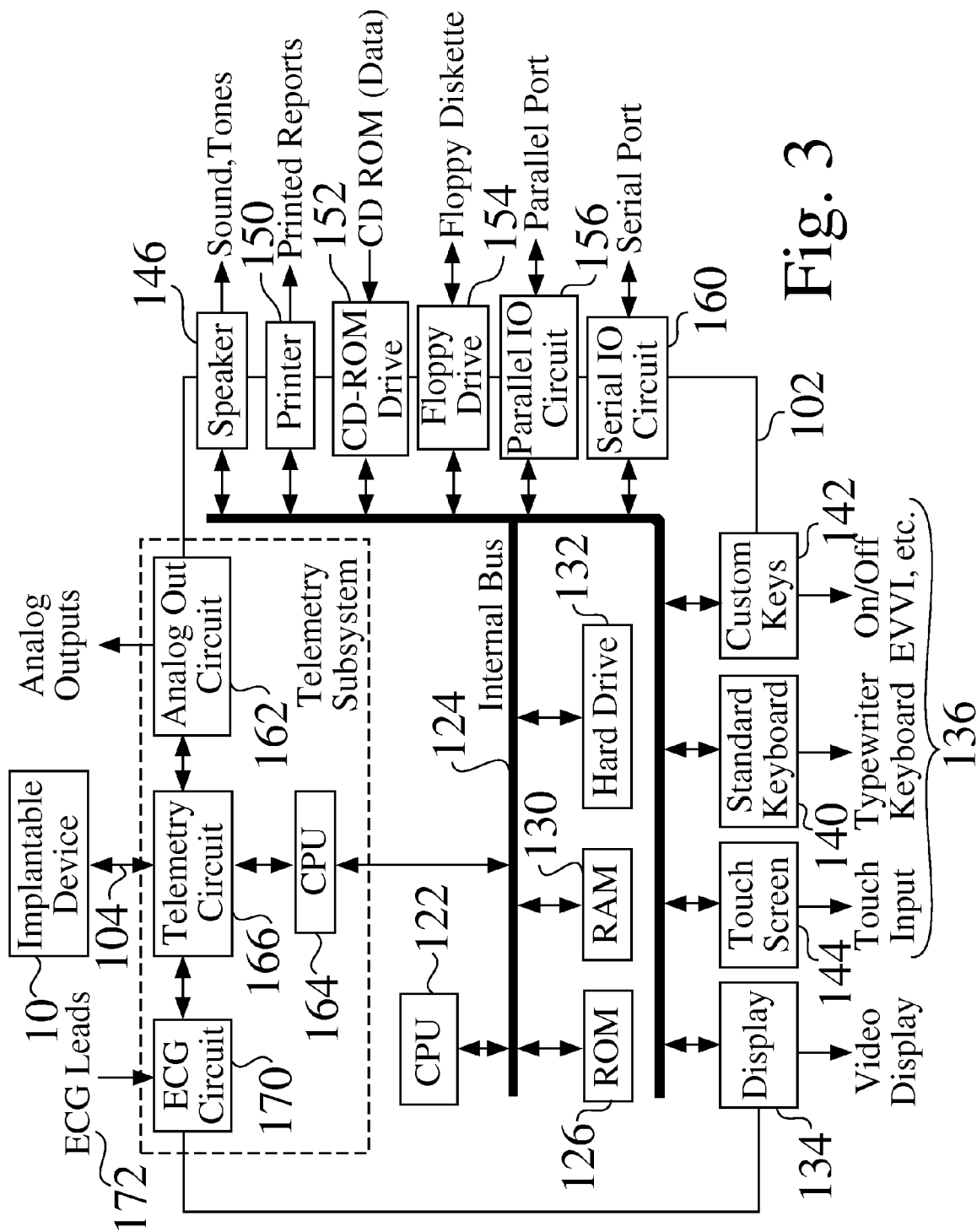
FIG. 3 is a functional block diagram of an external device capable of communicating with the implanted stimulation device when implanted, according to an embodiment of the device.

FIG. 3 is a functional block diagram of one embodiment of the external device 102, such as a physician's programmer. The external device 102 comprises a CPU 122 in communication with an external bus 124. The internal bus 124 provides a common communication link and power supply between various electrical components of the external device 102, such as the CPU 122. The external device 102 also comprises memory and data storage such as ROM 126, RAM 130, and a hard drive 132 commonly in communication with the internal bus 124. The ROM 126, RAM 130, and hard drive 132 provide temporary memory and non-volatile storage of data in a well known manner. In one embodiment, the ROM 126, RAM 130, and hard drive 132 can store control programs and commands for upload to the implantable device 10 as well as operating software for display of data received from the implantable device 10. It will be appreciated that in certain embodiments' alternative data storage/memory devices, such as flash memory, can be included or replaced one or more of the ROM 126, RAM 130, and hard drive 132 without detracting from the spirit of the invention.

The external device 102 also comprises a display 134. The display 134 is adapted to visually present graphical and alphanumeric data in a manner well understood in the art. The external device 102 also comprises input devices 136 to enable a user to provide commands and input data to the external device 102. In one embodiment, the input devices 136 include a keyboard 140, a plurality of custom keys 142, and a touch screen 144 aspect of the display 134. The keyboard 140 facilitates entry of alphanumeric data into the external device 102. The custom keys 142 are programmable to provide one touch functionality of predefined functions and/or operations. The custom keys 142 can be embodied as dedicated touch keys, such as associated with the keyboard 140 and/or predefined areas of the touch screen 144. In this embodiment, the external device 102 also comprises a speaker 146 and a printer 150 in communication with the internal bus 124. The speaker 146 is adapted to provide audible alert send signals to a user. The printer 150 is adapted to provide a printed readout of information from the external device 102.

In this embodiment, the external device also comprises a CD drive 152 and a floppy drive 154 which together provide removable data storage. In this embodiment, the external device also comprises a parallel input-output (IO) circuit 156, a serial IO circuit 160, and an analog output circuit 162. These circuits 156, 160, 162 provide a variety of communication capabilities between the external device 102 and other devices in a manner well understood in the art.

The external device 102 also comprises an electrocardiogram (ECG) circuit 170 in communication with a plurality of ECG leads 172. The ECG circuit 170 and the ECG leads 172 obtain electrical signals from the surface of a patient's body and configure the signals for display as an ECG waveform on the display 134 of the external device 102.

The external device 102 also comprises a telemetry CPU 164 and a telemetry circuit 166 which establish the telemetric link 104 in cooperation with the implantable device 10. The telemetric link 104 comprises a bidirectional link to enable the external device 102 and the implantable device 10 to exchange data and/or commands. As previously noted, the establishment of the telemetric link 104 is in certain embodiments facilitated by a wand or programmer head, which is placed in proximity to the implantable device 10. The wand or programmer head facilitates establishment of the telemetric link 104 by placing an antenna structure in a closer proximity to the implantable device 10 to facilitate conduction of transmitted signals to the external device 102.

The telemetric link 104 can comprise a variety of communication protocols appropriate to the needs and limitations of a given application. In certain embodiments, the telemetric link 104 comprises radio frequency (RF) telemetry. In one particular embodiment, the telemetric link 104 comprises a frequency modulated digital communication scheme wherein logic ones are transmitted at a first frequency A and logic zeros are transmitted second frequency B. As the implantable device 10 is powered by a battery having limited capacity and in certain embodiments the external device 102 is powered by line voltage, e.g., not subject to the stringent power limitations of the implantable device 10, the bidirectional telemetric link 104 can proceed in an asymmetric manner. For example, in one embodiment, a transmission power and data rate from the external device 102 to the implantable device 10 via the telemetric link 104 can proceed at higher power levels and/or higher data transmission rates than the reciprocal data rates and transmission power from the implantable device 10 to the external device 102. The telemetry circuit 100 of the implantable device 10 as well as the telemetry circuit 166 and CPU 164 of the external device 102 can select or be adjusted to provide a desired communication protocol and transmission power.

Figure 4:
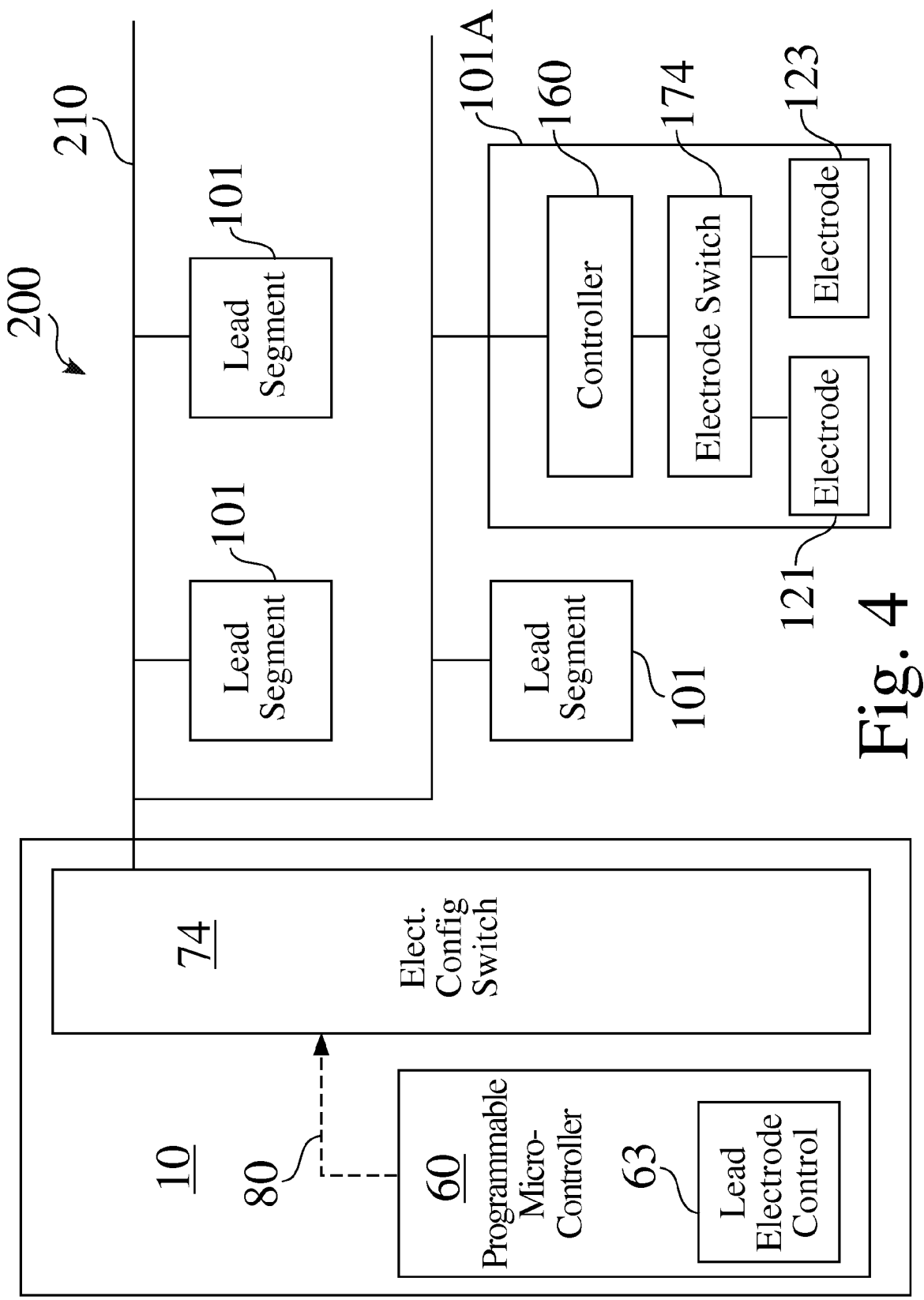
FIG. 4 is a functional block diagram of an implantable stimulation device connected to a lead forming a globe of electrodes illustrating the basic elements of the lead.

FIG. 4 shows a block diagram of the basic elements of a lead 200 connected to implanted device 10, according to an embodiment of the invention. The lead 200 comprises a bus 210 for transmitting control signals, sensed electrical signals, and therapeutic electrical stimulation. A number of lead segments 101 are connected to bus 210. Each lead segment 101 may comprise one or more electrodes that provide for sensing and delivering therapeutic stimulation to the heart, along with an integrated circuit containing control programming to activate and deactivate the electrodes of that lead segment 101. For example, lead segment 101A comprises two electrodes 121 and 123, along with a controller 160 and an electrode switch 174. Generally, electrodes located in the same lead segment are physically close to each other when implanted in the heart. Each of these electrodes may therefore be used to provide directional sensing and therapy. A spatial view of the activity of the heart is typically provided by electrodes at different lead segments, as will be described in more detail below.

The control circuit contained in each lead segment 101 allows for the bus 210 to require a relatively small amount of physical space for the wiring of multiple electrodes. In one embodiment, the bus 210 is a two-wire bus that controls 256 electrodes at 64 lead segments. The bus 210 carries signals between the implanted device 10 and each lead segment 101, including signals sensed by the electrodes, therapeutic electrical stimulation provided by the implanted device 10, and control signals provided by the lead electrode control 63 of the implanted device 10. In a preferred embodiment, lead segments 101 also receive power from implanted device 10 over bus 210.

Because a two-wire bus system must transmit all of these signals over the same wires, the control signals must be designed such that the sensed signals and therapeutic stimulations do not interfere with the control operations of the lead 200. Therefore, the control signal is generally a high-frequency signal. The control signal may be a frequency modulated digital communication scheme wherein logic ones are transmitted at a first frequency A and logic zeros are transmitted at a second frequency B, wherein A and B are substantially higher-frequency than the electrical signals generated in the heart or any therapeutic signals generated by implanted device 10. These control signals may identify each electrode by a unique control signal, and each combination of electrodes may additionally be identified by a unique control signal.

For example, electrode 121 may be identified for use in a unipolar mode with the case 40 acting as a return electrode by a signal representing the code '0001', while the electrodes 121 and 123 may be identified for use in a bipolar mode by a signal representing the code '1001'. These examples are for descriptive purposes only, and it will be understood that in other embodiments the control signals may vary, and may include additional information such as error correcting bits.

One embodiment of the operation of the lead 200 will now be described. Electrodes 121 and 123 of lead segment 101A may initially be inactive. In this state the electrodes 121 and 123 do not transmit sensed cardiac signals to implanted device 10, and do not receive therapeutic stimulation signals. The microcontroller 60 of implanted device 10 may send a control signal generated by lead electrode control 63 across bus 210 of lead 200. Each of the lead segments 101 will receive this control signal over bus 210. For example, the control signal may indicate that the electrode 121 is to be used in a unipolar mode for pacing applications with the case 40 acting as a return electrode. In another example, for ICDs, the return electrode could be another electrode in another lead. Thus, the control signal indicates that electrode 121 of lead segment 101A should be activated. Controller 160 of lead segment 101A will therefore instruct electrode switch 174 to activate electrode 121, which will then be electrically connected to implanted device 10 via bus 210. The controllers of the other lead segments 101 may either take no action after determining that the control signal indicates electrode 123 to be activated, or may in certain embodiments instruct the corresponding switch to deactivate or disconnect the electrodes of that lead segment depending upon the previous state of those electrodes.

When electrode 121 is active, it may be used to sense the electrical activity of the heart or to deliver therapeutic electrical stimulation from implanted device 10. When electrode 121 is sensing the electrical activity of the heart, the electric potential between the electrode 121 and the case 40 is measured and transmitted over bus 210 to implanted device 10. This received signal may be stored in memory 94 and analyzed by microcontroller 60.

When microcontroller 60 determines that a different electrode should be activated, another control signal may be generated by lead electrode control 63 and sent across bus 210. If this signal indicates that an electrode other than electrode 121 should be active, controller 160 of lead segment 101A will instruct electrode switch 174 to deactivate or disconnect electrode 121. In certain embodiments, the implanted device 10 may cycle through each electrode when sensing cardiac activity. For example, a different electrode (unipolar mode) or electrode combination (bipolar mode) may be activated every 100 microseconds. In other embodiments the system may activate certain electrodes for a longer or shorter period of time than 100 microseconds. The amount of time may be dependent, for example, on the amount of time it takes to transmit a control signal and operate electrode switch 174 in response to that signal. In other embodiments a shorter period is desired so that the system may cycle through each of the electrodes in less time.

The operation of lead 200 may be similar for providing therapeutic electrical stimulation in some embodiments to the operation described above for sensing the electrical activity of the heart. For example, a control signal may again be transmitted across bus 210, indicating that electrode 123 should be activated. When electrode 123 is activated by controller 160 and switch 174, the electrode 123 is connected to the implanted device 10. Therapeutic stimulations may then be generated by atrial pulse generator 70, ventricular pulse generator 72, or shocking circuit 116 depending on the therapy being provided. This electrical stimulation will be transmitted over bus 210 and delivered to the heart by electrode 123. After this stimulation has been delivered, another control signal may be generated to indicate a different electrode with which to continue the therapy. Which electrodes are activated to provide the therapy may be determined by microcontroller 60 of implanted device 10 according to certain embodiments of the invention that will be described later in more detail.

The foregoing description of a lead for use with some embodiments of the current invention is a simplified description that may be implemented in a number of ways as is known in the art. For example, each component, such as controller 160, may comprise a number of functional components. A more detailed description of a lead that may be utilized in some embodiments is described in U.S. Patent Publication No. 2006/0058588, titled "Methods and Apparatus for Tissue Activation and Monitoring," the entire contents of which are hereby incorporated by reference.

Figure 5:
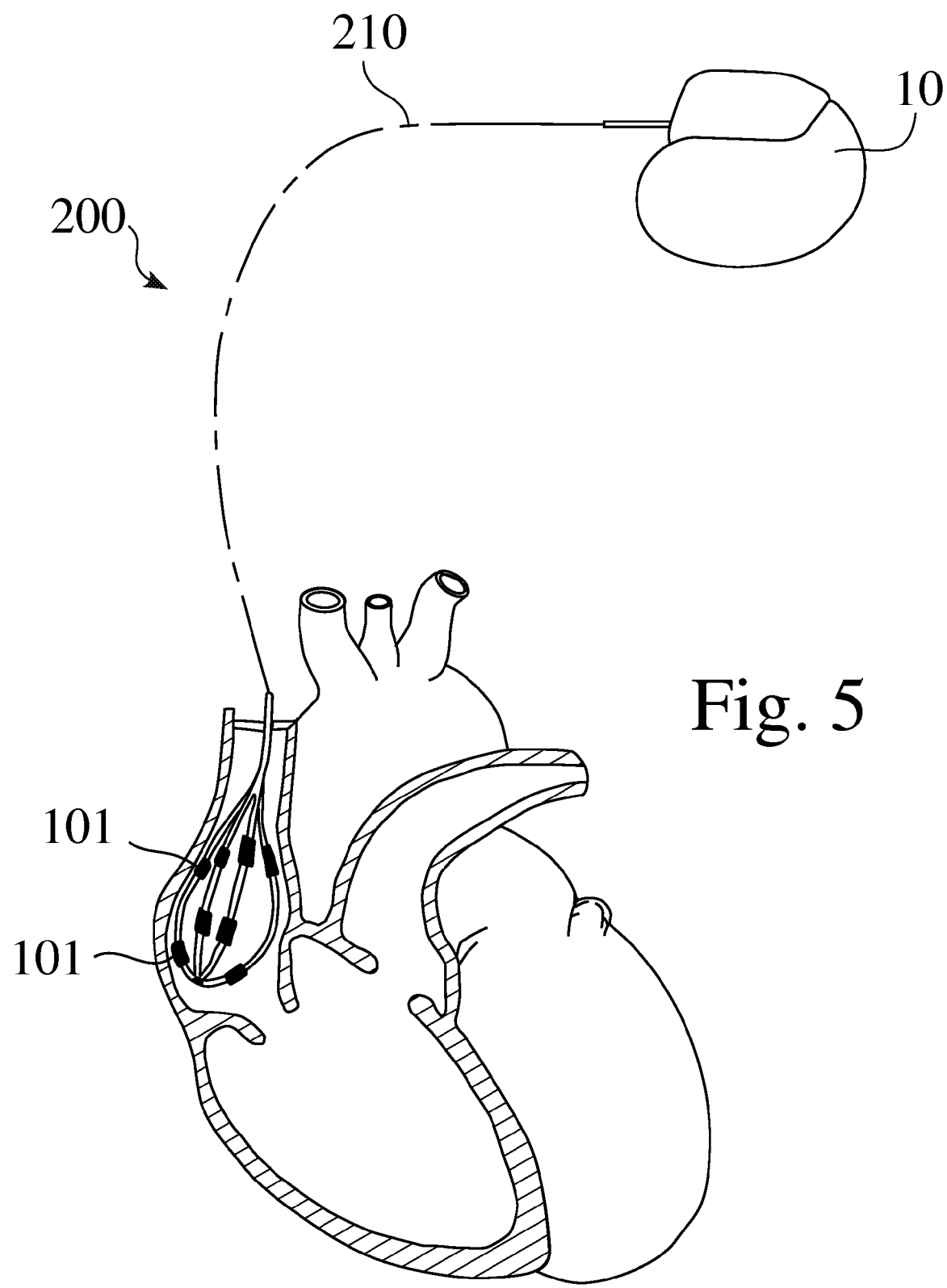
FIG. 5 is a simplified diagram illustrating an implantable stimulation device in electrical communication with a lead forming a globe of electrodes for measuring the electrical activity of the heart and for delivering therapeutic stimulation to the atrium.

FIG. 5 shows a simplified diagram of a lead 200 as described with reference to FIG. 4, for use with one embodiment of the current invention. The lead 200 shown comprises a plurality of lead segments 101 spatially distributed across the surface of the right atrium. Each lead segment 101 comprises one or more electrodes that are configured to be activated or deactivated utilizing control circuitry in each lead segment 101 and in response to a control signal provided by the microcontroller 60 of implanted device 10. When activated, each electrode or electrode pair may provide for sensing of the heart and stimulation therapy. In other embodiments, a similar lead is placed in the left atrium instead of or in addition to the lead shown. Similar leads may also be implanted into the ventricles of the heart in some embodiments.

The configuration of lead 200 may be referred to as a globe configuration or a globe of electrodes. This configuration approximates a spherical shape, though the contours of the lead are adapted to the shape of the chamber of the heart in which it is implanted, such as the right atrium. The globe shape is usually formed from a number of electrically connected 'rings'. The term 'ring' here is not equivalent to lead segment and is meant only to describe the shape of the lead. Generally, a ring may contain several lead segments. The electrodes contained in the lead segments of each ring may therefore deliver a substantially planar view of the activity of the heart. The combination of multiple rings allows for a spatially distributed 3-dimensional view of the activity of the heart. The lead 200 comprises two rings of electrodes, with each ring having four lead segments 101 for a total of eight lead segments of the lead 200. In other embodiments, different numbers of rings and lead segments may be used. In one embodiment of the invention, a lead comprises eight rings with eight lead segments on each ring. In another embodiment, a lead comprises four rings with eight lead segments on each ring. In certain embodiments, a lead utilizing a similar control and communications interface is utilized, but is not configured to have rings. For example, the lead may be approximately linear when implanted and follow a path similar to any of those shown in FIG. 1 for the leads 20, 24, and 30.

The globe configuration of lead 200 allows for a number of advantages over standard leads. The configuration allows for a relatively high number of electrodes, and therefore generally provides more data to the implanted device 10 than a standard lead. For example, a globe configuration may contain 256 electrodes in 64 lead segments, compared with a standard lead which may provide three electrodes, such as a tip, ring, and coil electrodes. Additionally, the globe of electrodes configuration shown provides for electrodes that are distributed spatially in three-dimensions in the heart, as opposed to standard leads which approximate a linear representation of the heart. These advantages may be utilized as described in more detail below to provide efficient sensing and therapy.

FIGS. 4 and 5 show a single lead 200 connected to implanted device 10, according to one embodiment of the invention. However, multiple leads may be connected to implanted device 10. For example, lead 200 may be connected to implanted device 10 in addition to leads 24 and 30 shown in FIG. 1. In other embodiments, multiple globe configuration leads may be connected to implanted device 10. In some such embodiments implanted device 10 may further comprise additional circuitry such as a multiplexing circuit controlled by lead electrode control 63 and connected to each globe configuration lead so that the implanted device 10 uses a single control signal to activate the selected electrodes on any of the attached globe configuration leads. Alternatively, each globe configuration lead may be controlled individually.

In addition to the globe configuration lead similar to that described above, it may also be possible to obtain location information with other lead configurations. In some of these embodiments, a right atrial lead 20 is used having an atrial tip electrode 22 and three atrial ring electrodes 21, 23, and 25, as shown in FIG. 1. In this embodiment, microcontroller 60 provides control signals to electrical configuration switch 74 to activate terminals 41, 42, 43, and 45 when it determines which of electrodes 21, 22, 23, and 25 to utilize for sensing or therapy. Thus, implanted device 10 can sense the electrical activity of the heart from these electrodes, and may also provide therapeutic electrical stimulation in the same manner as described above. While electrodes 21, 22, 23, and 25 may not provide as much data as the globe configuration lead discussed above, the electrodes 21, 22, 23, and 25 are nonetheless spatially distributed to allow for an approximation of the location of an irritable focus, as will be described below.

An implanted device such as those described above typically functions to both sense the electrical activity of the heart and to provide therapeutic electrical stimulation when necessary. While the heart is functioning normally, the device will typically act only to sense the activity of the heart and may store data relating to this activity. A normal cycle of the heart may begin when an electrical signal is generated in the SA node of the heart. A resulting depolarization wave then propagates through the atria, and in turn causes the activation of the AV node. From the AV node, an electrical signal is spread through the right and left ventricles. The depolarization and corresponding repolarization cause the contraction of the chambers of the heart, resulting in the movement of blood through the body. When the heart is functioning normally, this activity occurs regularly at a rate of approximately 60 to 100 beats per minute. An implanted device generally determines when this activity is occurring properly by measuring the electric potential between an active electrode and a return and detecting the depolarization wave at different locations in the heart. For example a potential is measured between an electrode located in the right atrium and the case 40. A change in the electric potential generally reflects a depolarization wave reaching the electrode, such as the depolarization wave initiated by the regular activity of the SA node.

When a tachycardia is present, the heart may not be functioning properly. The heart may be beating at a higher or lower rate than normal. In some cases this may not be harmful. For example, the heart may beat more rapidly during heavy exercise. However, in some cases a tachycardia represents a dangerous condition. When one or more chambers of the heart are beating at a consistently high rate, the movement of blood through the body is inefficient. This can increase, for example, the risk of blood stagnation and stroke. Implanted devices generally may detect these conditions by sensing the higher-frequency depolarization waves associated with an increased heart rate. These devices also may consider, for example, the rate at which the heart rate changed in determining whether or not a detected condition is dangerous and requires treatment.

Examples of dangerous conditions that may be detected are atrial fibrillation and atrial flutter. Both of these conditions originate in the atria and result in a rapid heart rate in the chambers of the atria. Atrial fibrillation is typically associated with atrial heart rates in excess of 400 beats per minute and atrial flutter is typically associated with atrial heart rates of approximately 300 beats per minute. The resulting heart rate in the ventricles may or may not be high, because the AV node functions to block electrical impulses occurring faster than a certain rate. For example, atrial flutter is often associated with either a 2:1 block or a 4:1 block, typically resulting in a ventricular rate of approximately 150 beats per minute or 75 beats per minute, respectively. The cause of these conditions is often one or more irritable foci. An irritable focus is an area in the heart that is generating abnormal electrical signals, overriding the electrical signals generated by the SA node. In atrial fibrillation these irritable foci generally provide regular high rate electrical signals, while with atrial flutter the electrical signals are disorganized. In both cases, the resulting rapid heart rate may be dangerous or, at a minimum, significantly decrease the ability of the heart to provide blood to the patient's organs and tissues.

Typical treatment provided by an implanted device may include providing therapeutic electrical stimulation. In this treatment, the implanted device uses the electrodes located in the appropriate chamber of the heart to provide a series of shocks. These shocks are usually at a programmed frequency and energy level to eventually override the irritable foci and return the heart to a normal rate.

While this treatment may be effective, it is not necessarily provided in the most efficient manner to terminate an atrial arrhythmia such as atrial fibrillation or atrial flutter. For example, while typical systems take into account factors such as a defibrillation threshold to assure that the treatment is effective, they are not able to account for other important factors such as the location of the irritable foci responsible for the atrial arrhythmia. According to those systems, a condition originating at one location in the heart may be treated nearly identically to a condition originating at a different location.

According to novel aspects of one embodiment of the current invention, the general or approximate locations of irritable foci responsible for an atrial arrhythmia are determined. The locations may be obtained, for example, by analyzing the different times at which electrical signals indicative of a cardiac event are detected by a plurality of electrodes spatially distributed within a chamber of the heart. Once the location is obtained, it may be used by an implanted device to deliver therapeutic stimulation, such as an ATP pulse train, to more efficiently to treat the condition. For example, the device may focus electrical stimulation in the electrodes nearest the location of the irritable foci, or along a vector that is determined to be effective in providing therapy to the irritated focus or source of the atrial arrhythmia. This may provide for faster termination of the atrial arrhythmia. Thus, patient comfort and device longevity may be increased by reducing the quantity of therapeutic stimulations while simultaneously reducing health risks by resolving dangerous conditions more quickly.

Figure 6:
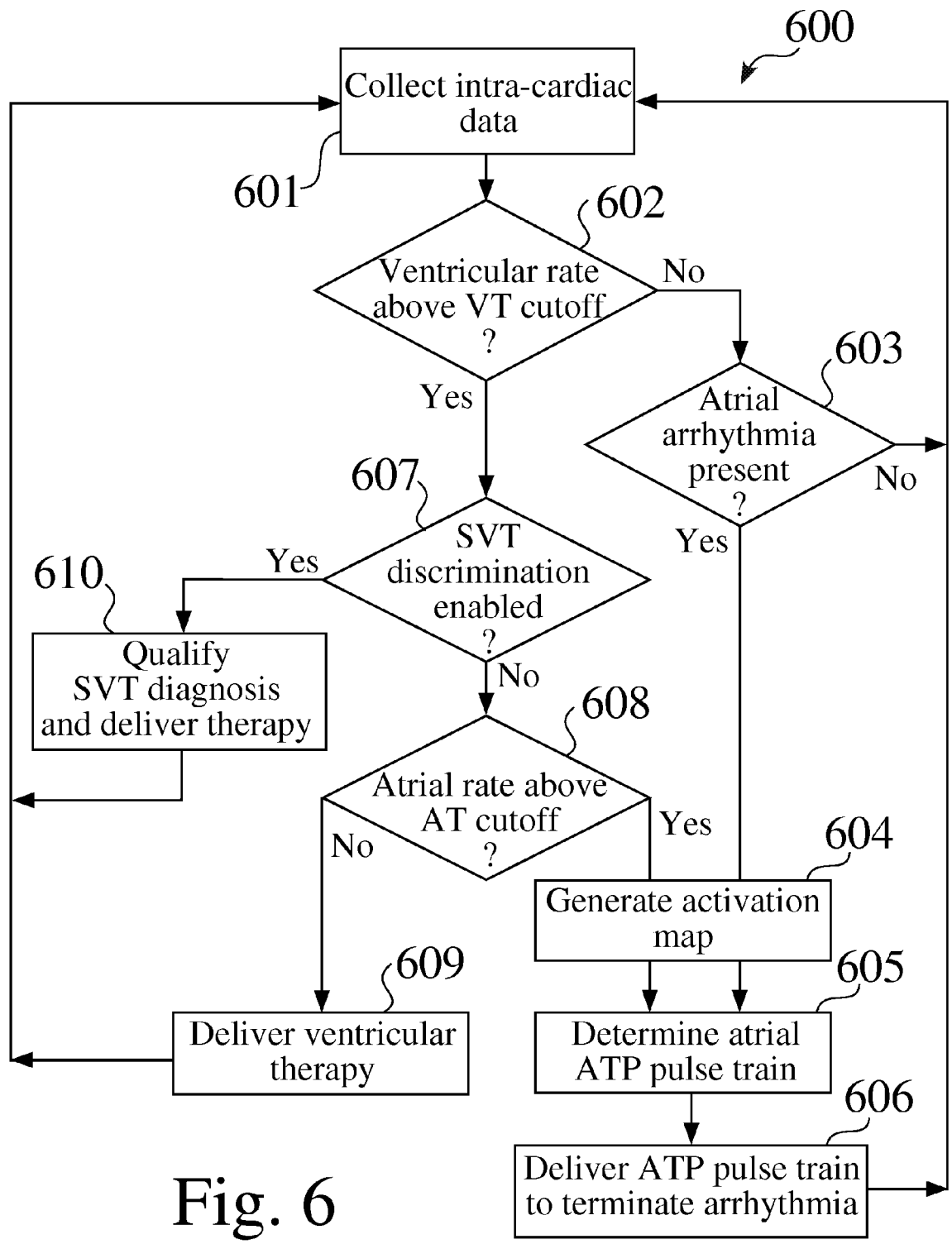
FIG. 6 is a flow chart describing an overview of the operation for identifying and treating abnormal electrical activity in the atrium, according to an embodiment of the invention.

FIG. 6 is a flow chart describing the operation and novel features of an implanted device 10 according to an embodiment of the current invention. In the flow chart 600, the various algorithmic steps are summarized in individual "blocks". Such blocks are exemplary of the actions or decisions made or carried out as the algorithm proceeds. A person of ordinary skill in the art will recognize that the actual implementation of the process can be accomplished many of a number of ways without departing from the spirit or scope of the present invention.

In an embodiment where a microprocessor 60 (or equivalent) is employed, the flow chart presented herein provides the basis for a "control program" that can be used by such a microprocessor 60 to effectuate the desired control of the implanted device 10. In other embodiments, portions of the control program can be used by CPU 122 of the external device 102 to generate data and control signals, and to effectuate the desired control of implanted device 10. Those skilled in the art may readily write such a control program based on the flow chart 600 and other descriptions presented herein.

FIG. 6 displays an overview of the process 600 for detecting and treating a tachycardia, according to one embodiment of the invention. Throughout the description of this embodiment of process 600, reference is made to FIGS. 1-5 and their components. These references are made for descriptive purposes only, and are not intended to limit the scope of the invention. Devices and processes that vary from those shown or described may be utilized without departing from the spirit of the invention.

At state 601, the implanted device 10 collects intra-cardiac data from the lead electrodes. For example, the implanted device 10 may measure the electrical signal between the first right atrial ring electrode 21 and the case 40. The implanted device may substantially simultaneously sense the electrical signal between right ventricular tip electrode 32 and right ventricular ring electrode 34. In preferred embodiments, the implanted device 10 may utilize a globe of electrodes as shown in FIG. 5, and may cycle through the electrodes to measure the electrical activity of the heart. Implanted device 10 may store data collected in memory 94 either for later retrieval by a physician or for short-term analysis of, for example, the rate of change of the heart rate. In the latter case, data may be stored on a temporary basis and overwritten by later collected data to conserve space in memory 94. Process 600 proceeds from state 601 to decision block 602.

At decision block 602, the microprocessor 60 of the implanted device 10 determines if the ventricular rate is above a programmed ventricular tachycardia cutoff rate (VT cutoff). Accordingly, electrodes in the ventricles may detect a ventricular heart rate. If this rate is above some set VT cutoff, a ventricular tachycardia is determined to exist. The VT cutoff may, for example, be approximately 100 beats per minute. In some embodiments, the limit depends on specific patient characteristics such as age. In other embodiments, the VT cutoff may vary for an individual patient. The cutoff need not be compared against the instant ventricular rate. For example, a moving average ventricular rate may be compared against the VT cutoff in some embodiments. If the rate is above the VT cutoff, the process 600 proceeds to decision block 605. Otherwise, the process 600 proceeds to decision block 603.

At decision block 603, implanted device 10 determines if an atrial arrhythmia is present. In one embodiment of the invention, this step is accomplished in a manner similar to decision block 602, except that the atrial rate is compared to an atrial tachycardia cutoff rate (AT cutoff). Thus, an atrial arrhythmia may be found where the atrial rate is greater than 100 beats per minute in some embodiments. The atrial rate may be determined by utilizing the electrodes implanted in either or both chambers of the atria to detect a frequency of cardiac electrical activity. In one embodiment, the rate compared against the cutoff is a moving average of the atrial rate as determined by a filtered atrial rate interval. In some embodiments the AT cutoff is some other rate other than 100 beats per minute and may depend on patient specific characteristics. In some embodiments, other factors are used to determine whether an atrial arrhythmia is present, such as the rate at which the atrial rate increased. If it is determined at decision block 603 that an atrial arrhythmia is not present, then the process 600 returns to state 601 and continues collecting intra-cardiac data. If an atrial arrhythmia is found, then process 600 proceeds to state 604.

At state 604, an activation map is generated. The microprocessor 60 or a functional activation map generator is configured to generate the activation map using sensed intra-cardiac data. The activation map provides the implanted device 10, and in some embodiments an external device 102, with an approximation of the location of the region of the heart, e.g. the irritable foci, responsible for an atrial arrhythmia. In one embodiment, a globe configuration lead is utilized in collecting intra-cardiac data to provide spatially distributed data for activation map generator or microprocessor. As opposed to standard leads, a globe configuration lead may provide a substantially three-dimensional view of the electrical activity of the heart, which may increase the accuracy of the activation map. In other embodiments, a standard lead may be used with a plurality of electrodes. Once the activation map has been generated, the process 600 continues to state 605.

At state 605, a therapy is determined. The microcontroller 60 utilizes the activation map generated in the previous step to determine the appropriate therapy, such as ATP pulse train therapy. The therapy is determined, for example, so that a relatively efficient electrical stimulation therapy can be applied to override the activity of the irritable foci responsible for the atrial arrhythmia. In some embodiments, the therapeutic electrical stimulation comprises an ordered delivery of electrical stimulations to less than all of the electrodes on a lead located in the appropriate chamber of the heart. In other embodiments each electrode may be used to provide electrical stimulation to the heart, as well as electrodes located in multiple chambers of the heart. The microcontroller 60 may further configure the timing between pulses at the selected electrodes and the strength of each shock according to different embodiments. Thus, the microcontroller 60 may in one implementation configure a vector or direction, a magnitude, and a frequency for each part of the electrical stimulation therapy.

In some embodiments, the implanted device 10 may focus therapeutic electrical stimulations in electrodes near the location of the irritable foci identified in the activation map. These electrodes may be determined by comparing the activation map generated at state 604 with stored information describing the location of the implanted electrodes. In a preferred embodiment, a globe configuration lead is used so that there are likely to be a number of electrodes near the location of any irritable foci responsible for abnormal electrical activity in the heart. In other embodiments, the electrodes used to provide the therapy may be determined along a vector that is found to efficiently treat a condition originating at the known location of the irritable foci. In some embodiments, this vector approximates the known internodal tracts that transmit the regular stimulation of the heart from the SA node to the AV node.

At state 606, the determined therapy, such as an atrial ATP pulse train, is delivered through the implanted lead or leads. The therapy may continue to be delivered, for example, until the delivered electrical stimulation overrides the irritable foci and the atrial arrhythmia is terminated. In some embodiments, the therapy may be delivered for a specified amount of time. In certain embodiments, the process 600 may begin again while the therapy is being delivered or between shocks. In these and other embodiments, the therapy may be modified based on information detected by the leads of implanted device 10. In some embodiments the therapy is repeated at a regular rate greater than the current atrial rate. In other embodiments therapeutic stimulation is delivered at a regular rate less than the current atrial rate. The process 600 returns to state 601 when the atrial arrhythmia is terminated.

Returning to decision block 602, if the ventricular rate is above the VT cutoff then the process 600 proceeds to decision block 607. At decision block 607 it is determined whether or not subventricular tachycardia (SVT) discrimination is enabled. SVT discrimination may allow implanted device 10 to determine whether the source of the ventricular tachycardia is ventricular or instead originates in either the atria or the pulmonary veins. If SVT discrimination is enabled, then process 600 continues to state 610. Otherwise, process 600 moves to decision block 608.

Decision block 608 determines whether or not the atrial rate is above an AT cutoff rate. In some embodiments, this step is similar to the process described at decision block 603. For example, a moving average of the atrial rate may be compared to some predetermined or variable AT cutoff. Because SVT discrimination is not enabled, this step may allow for the determination of whether a ventricular tachycardia may actually originate in the atria, and therefore require pacing at that location rather than in the ventricles. If it is determined that the atrial rate exceeds the AT cutoff, then the source of the tachycardia is likely the atria, and process 600 proceeds to state 604, 605, and 606. Accordingly, an activation map is generated and a therapy is determined and delivered to terminate the arrhythmia. If the atrial rate does not exceed the cutoff, then process 600 proceeds to state 609. At state 609, ventricular therapy is delivered by implanted device 10. In some embodiments, this therapy is standard electrical stimulation therapy and pacing. In other embodiments, this therapy may include mapping the ventricles and delivering an optimized pulse train similar to the method described with respect to treating atrial arrhythmias. Process 600 then returns to state 601 and again collects intra-cardiac data.

If SVT discrimination is enabled at decision state 607, the process 600 generates an activation map to qualify the SVT diagnosis and delivers appropriate therapy at state 610. The activation map may be generated in a fashion similar to that described at state 604. The activation map may then indicate, for example, that an atrial source is or is not causing the ventricular tachycardia. If the activation map confirms the SVT diagnosis, then therapeutic pacing may be provided to the indicated area of the heart only. If the activation map disagrees with the SVT diagnosis, then pacing may be provided in multiple areas of the heart or not at all, depending on the exact conditions and the device programming for the particular patient. In this way, the SVT diagnosis is confirmed to ensure accuracy. Thus, the system is more likely to provide all of the treatment that is necessary and is also more likely to not provide excess shocks, which may be uncomfortable to the patient. Once the detected ventricular tachycardia has been treated, the process 600 again returns to state 601.

Figure 7:
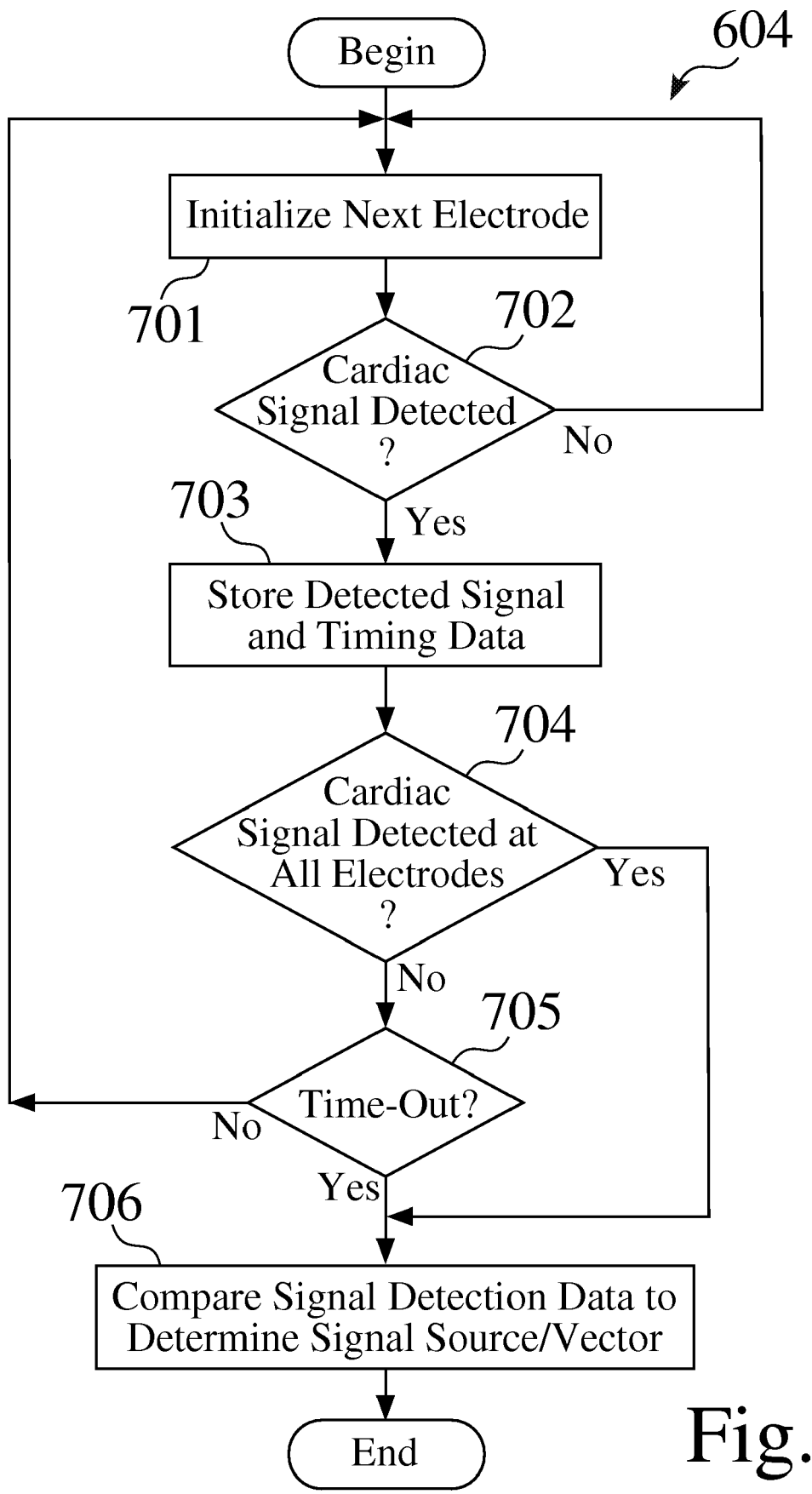
FIG. 7 is a flow chart describing an overview of the operation for mapping the electrical activity of the heart using a plurality of spatially distributed electrodes, according to an embodiment of the invention.

FIG. 7 shows a more detailed view of one embodiment of the process 604 for generating a map of the electrical activity of the heart. As with process 600, process 604 is shown with exemplary function blocks. Such blocks represent one embodiment of the process 604. It will be recognized that the actual implementation of the process 604 can be accomplished in a variety of ways without departing from the spirit of the invention.

The process 604 typically describes mapping activity in one chamber of the heart, such as either the left or right atrium. Thus, in some embodiments, cycling through electrodes may occur substantially for electrodes within the given chamber of the heart. In other embodiments, signals from multiple chambers of the heart may be used to map the electrical activity of the heart.

Process 604 begins at state 701 where an electrode is initialized. For example, electrode 121 of lead segment 100A on lead 200 may be initialized. Electrode 121 may be initialized by sending a high-frequency control signal generated by lead electrode control 63 across lead 200. Each of the lead segments 101 of lead 200 may receive such a signal, and only the appropriate electrodes would be activated. When electrode 121 is initialized, it transmits sensed electrical activity of the heart to implanted device 10. In other embodiments, each electrode may be connected directly to a terminal of implanted device 10. For example, three atrial ring electrodes 21, 23, and 25 may be connected to terminals 41, 43, and 45 of device 10, as shown in FIGS. 1 and 2. In some of these embodiments, the controller 60 may receive sensed electrical signals from these electrodes substantially simultaneously. In other embodiments, the step of initializing an electrode comprises sending a control signal to electrical configuration switch 74 to connect the appropriate terminal of implanted device 10 with the controller 60. When a sensed electrical signal is being transmitted from the selected electrode to implanted device 10, the process 604 continues to decision block 702.

At decision block 702, the process 604 determines if a cardiac signal event is detected, according to one embodiment. Generally, a cardiac signal event is the generation of an electrical signal within the heart. For example, the controller 10 determines if the signal sensed by the selected electrode indicates that a depolarization wave originating in the heart has reached the electrode. A variety of methods for detection of such an event are known in the art. For example, a change in the electric potential may be identified at the electrode. If no cardiac signal event is detected at decision block 702, then the process 604 returns to state 701 and initializes the next electrode. If a cardiac signal event, such as a depolarization wave, is detected at decision block 702, then the process 604 proceeds to state 703.

At state 703, data surrounding the detected cardiac signal event is stored in memory 94 of implanted device 10. The stored data may comprise, for example, information indicating the time or relative time that the depolarization wave reached the selected electrode. In other embodiments, this step is performed by substantially continuously storing the signal detected by each electrode and analyzing recent data to determine when a depolarization wave reached each electrode. In one embodiment, recent data includes data collected within a time corresponding to approximately one heartbeat.

Proceeding to decision block 704, the process 604 determines if the cardiac signal event has been detected at each of the electrodes. If the cardiac signal event has been detected, then the process 604 may proceed to analyze the information at state 706. If not, then the process may proceed to decision block 705. In other embodiments, implanted device 10 does not attempt to determine if a cardiac signal event has been detected in each electrode. In these embodiments, the implanted device 10 may analyze a given amount of data, without first determining if a cardiac signal event has been detected by each electrode. For example, implanted device 10 may determine an approximate heart rate of the appropriate chamber and analyze data corresponding to at least one heart beat.

If process 604 does determine whether a cardiac signal event has been detected at each electrode in decision block 704 and such an event has not been detected at all of the electrodes, then the process proceeds to decision block 705. At decision block 705 it may be determined if enough time has passed that the process will no longer wait for the cardiac signal event to be detected. For example, process 604 may wait for a time corresponding to at least one heartbeat. If no cardiac signal event is detected in the given time, it may be assumed in some embodiments that the cardiac signal event will not reach those electrodes. Thus, if there is a time-out, the process 604 will proceed to state 706 and the collected data from each electrode will be analyzed. If the system has not timed-out, then the process 604 may return to state 701 and initialize the next electrode.

At state 706, whatever data has been collected will be analyzed to determine the cardiac signal event origin. In one embodiment of the invention, this will involve comparing the relative times at which the cardiac signal event reached each electrode. In general, the differences in the times at which each electrode detects the cardiac signal event will represent a difference in the distance from the source of the event. Thus, the electrode that first detects the cardiac signal event may be the closest to the point of origin. In some cases, this may not be the case. For example, the electrical characteristics of different areas of the heart may affect the rate of propagation of a signal. Therefore, some embodiments include storing data related to the electrical characteristics of different areas of the heart in memory 94 for use by activation map generator 61.

Another method that may be used in some embodiments to aid in determining the location of a cardiac signal event origin is comparing the magnitude of detected electrical signals to determine the direction of the depolarization wave vector. For example, when two electrodes are located at an approximately equal distance to the origin of a signal and are arranged substantially perpendicular to the signal vector, the voltage between the two electrodes will have a relatively small magnitude because the signal will reach each of the electrodes at approximately the same time. In contrast, electrodes located substantially along the path of the signal vector will tend to have a relatively large magnitude potential difference between them, because the signal will reach one site substantially before the other. Thus, the arrangement of the electrodes may be utilized to help approximate the direction of the signal propagation.

The implanted device 10 has at least some data related to the location of each of the electrodes stored in memory 94. Thus, activation map generator 61 may utilize this data, along with the intra-cardiac data measured by the electrodes, to determine the location of irritable foci relative to these electrodes.

Different embodiments of the current invention have been discussed with reference to using an activation map for providing a therapeutic electrical stimulation. However, an activation map may be used for other purposes as well. In some embodiments, one or more activation maps are stored in memory 94. These activation maps may be transmitted to external device 102 using telemetry circuit 100. This may be useful, for example, in providing a physician with information identifying the approximate location responsible for any atrial arrhythmia that has affected the patient, without requiring surgery. Such information may be used to determine if one area is consistently responsible for an atrial arrhythmia and therefore prepare the physician to perform an ablation procedure.

As can be seen, the different embodiments discussed herein provide a number of advantages over the prior art. In some embodiments, a system is provided that allows for the mapping of the heart by an implanted device. This information may be used by the implanted device to provide more efficient treatment. Thus, one advantage realized by some of the disclosed embodiments is the ability to more efficiently treat atrial arrhythmias by providing less therapeutic stimulation while still terminating the condition more quickly than other some other methods. In some embodiments, the system determines more optimal electrical stimulation therapy to provide this efficient treatment. In some embodiments, the implanted device is able to transmit stored electrical activation map information to an external device that may advantageously be used to approximate the location of irritable foci before an ablation procedure. This information may be provided before the procedure without requiring implantation of additional leads. While certain advantages have been described, other advantages may be obtained using certain embodiments described above. Furthermore, not every embodiment may offer all of the advantages described. Nonetheless, those embodiments may be practiced without departing from the spirit of the invention.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

What is claimed is:

1. An implantable cardiac stimulation device comprising:
   at least one lead adapted to be implanted proximate to the atrial walls of the heart;
   a plurality of electrodes coupled to the at least one lead so as to be spatially distributed with respect to the atrial walls of the heart, wherein the plurality of electrodes both sense electrical activity of the heart and also are adapted to provide therapeutic stimulation to the heart;
   a controller that receives signals indicative of the electrical activity of the heart from the plurality of electrodes and selects at least one electrode for the delivery of therapeutic stimulation to the heart, wherein the controller detects the existence of a supra-ventricular tachycardia event based upon the signals received from the plurality of electrodes and in response to detecting the existence of a supra-ventricular tachycardia, sequentially senses the supra-ventricular tachycardia from at least some of the plurality of electrodes that are spaced from each other and determines an appropriate electrical stimulation therapy, and selects at least one of the plurality of electrodes to deliver at least one electrical stimulation to the heart based upon the determined appropriate electrical stimulation therapy wherein the controller uses the signals from the plurality of electrodes that are spaced from each other to map location information about the origin of the supra-ventricular tachycardia.

2. The system of claim 1, wherein the plurality of electrodes comprises a right atria tip electrode, a first right atrial ring electrode, and a second right atrial ring electrode.

3. The system of claim 1, wherein the plurality of electrodes forms a spatially distributed globe of electrodes positioned within the atrium.

4. The system of claim 3, wherein the globe of electrodes comprises a plurality of lead segments, and wherein each lead segment comprises at least one local electrode and an electrode controller that is configured to activate or deactivate the at least one local electrode.

5. The system of claim 4, wherein the electrode controller is configured to receive a high-frequency signal that induces the electrode controller to activate the at least one local electrode.

6. The system of claim 1, wherein the controller determines the existence of a supra-ventricular tachycardia event by comparing an atrial tachycardia cutoff rate with a moving average atrial rate determined by using the signals received from the plurality of electrodes.

7. The system of claim 6, wherein the atrial tachycardia cutoff rate is approximately 170 beats per minute.

8. The system of claim 1, further comprising a multiplexing device that, upon the controller determining the existence of a non-ventricular tachycardia event, sequentially senses the supra-ventricular tachycardia event from the plurality of electrodes.

9. The system of claim 1, wherein the controller determines the location information of the source of the supra-ventricular tachycardia event by evaluating at least in part the relative timing of the signals received at each of the plurality of electrodes.

10. The system of claim 1, wherein the controller, upon determining the location information of the supra-ventricular tachycardia, uses the location information to select an electrode pair to provide therapeutic stimulation to attempt to inhibit the supra-ventricular tachycardia.

11. The system of claim 10, wherein the controller determines the location information of the source of the non-ventricular tachycardia event by comparing the relative timing of the signals received at each of the plurality of electrodes with the electrical characteristics of the heart to determine an approximate distance from each of the plurality of electrodes to the source of the non-ventricular tachycardia event and comparing these approximate distances to a known approximate location for each electrode to determine the source of the non-ventricular tachycardia event.

12. The system of claim 10, wherein the location information is stored for subsequent downloading to an external device.

13. An implantable device capable of measuring cardiac activity and providing stimulation to a patient's heart, comprising:
   a processor;
   a memory;
   a housing in which the processor and the memory are mounted wherein the housing is configured to be implanted into a patient's body;
   a plurality of electrodes located external to the housing, wherein each electrode is adapted to transmit a signal indicative of an intrinsic electrical signal originating in the heart to the processor and each electrode is adapted to provide an electrical stimulation to the heart; and
   wherein the processor sequentially samples at least some of the plurality of electrodes in response to detecting the signal indicative of the intrinsic electrical signal and is capable of mapping location information about a source of the intrinsic electrical signal within the heart based upon a plurality of signals received by the processor from the sampled plurality of electrodes corresponding to the intrinsic electrical signal and storing a first set of data representing the location information about the source of the intrinsic electrical signal in the memory, wherein the processor is adapted to determine an appropriate electrical stimulation therapy based at least in part upon the location information about the source of the intrinsic electrical signal, and the processor is further adapted to induce at least one of the plurality of electrodes to deliver at least one electrical stimulation to the heart based upon the determined appropriate electrical stimulation therapy.

14. The system of claim 13, further comprising a telemetry device located in the housing and connected to the processor, wherein the telemetry device is adapted to transmit data to an external device, wherein the data is indicative of the first set of data representing the location information of the source of the intrinsic electrical signal.

15. The system of claim 13, wherein the determined electrical stimulation therapy comprises therapy that will be provided by at least one electrode determined to be relatively near the source of the intrinsic electrical signal.

16. The system of claim 13, wherein the plurality of electrodes comprise a right atrial tip electrode, a first right atrial ring electrode, and a second right atrial ring electrode.

17. The system of claim 13, wherein the processor is configured to deliver at least one electrical stimulation to the heart when the intrinsic electrical signal is determined by the processor to be indicative of an atrial tachycardia event.

18. The system of claim 13, wherein the plurality of electrodes form a spatially distributed globe of electrodes.

19. The system of claim 18, wherein the globe of electrodes comprises a plurality of lead segments, and each lead segment comprises at least one local electrode and an electrode controller configured to activate or deactivate the at least one local electrode.

20. The system of claim 19, wherein the processor is configured to generate a control signal that induces the electrode controller of one of the plurality of lead segments to activate one of the corresponding local electrodes.

21. The system of claim 13, further comprising a multiplexing device that sequentially senses the first electrical stimulation from the plurality of electrodes.

22. The system of claim 21, wherein the multiplexing device receives a high frequency signal that induces the multiplexing device to sense the first electrical stimulation from a plurality of different electrode pairs.

23. The system of claim 22, wherein the multiplexing device samples first electrical stimulation originating in the heart at each electrode pair at approximately 100 microsecond intervals.

24. The system of claim 13, wherein the processor determines the location information about the source of the intrinsic electrical signal originating in the heart by comparing the relative timing of the signals indicative of the first electrical stimulation transmitted to the processor by each of the electrodes.

25. The system of claim 24, wherein the processor determines the location information about the source of the intrinsic electrical signal originating in the heart by comparing the relative timing of the signals indicative of the first electrical stimulation transmitted to the processor by each of the electrodes with the electrical characteristics of the heart to determine an approximate distance from each of the plurality of electrodes to the source of the intrinsic electrical signal and comparing these approximate distances to a known approximate location for each electrode to determine source information about the intrinsic electrical signal.

26. A method for approximating an origin of an electrical signal generated in a heart utilizing an implanted device including a plurality of electrodes spatially distributed in a chamber of the atria, comprising:

determining whether the intrinsic electrical signal indicative of an atrial tachycardia has been detected by the plurality of spatially distributed electrodes;

in response to determining that an electrical signal indicative of an atrial tachycardia has occurred, sequentially sampling at least some of the spatially distributed plurality of electrodes to obtain information about the intrinsic electrical signal indicative of an atrial tachycardia by selectively activating electrodes for discrete time periods following the detection of an event;

storing timing information about when the intrinsic electrical signal was detected by the at least some of the plurality of spatially distributed electrodes when it is determined that the intrinsic electrical signal has been detected;

using the timing information about when the intrinsic electrical signal indicative of an atrial tachycardia was detected by each of the at least some of the plurality of electrodes in conjunction with location information of each of the plurality of electrodes to map the origin of the intrinsic electrical signal indicative of the atrial tachycardia.

27. The method of claim 26, wherein the plurality of electrodes comprise a right atrial tip electrode, a first right atrial ring electrode, and a second right atrial ring electrode.

28. The method of claim 26, wherein the plurality of electrodes form a spatially distributed globe of electrodes, and wherein the globe is formed from a plurality of rings and each ring contains at least one of the plurality of electrodes.

29. The method of claim 26, further comprising the step of determining a vector associated with an approximate direction of propagation of the intrinsic electrical signal indicative of the atrial tachycardia through the heart.

30. The method of claim 29, wherein the step of determining a vector utilizes the timing information about when the intrinsic electrical signal indicative of the atrial tachycardia was detected by each of the plurality of electrodes and a second set of data corresponding to a magnitude of the electrical signal that was detected by each of the plurality of electrodes.

31. The method of claim 30, wherein the step of comparing timing information about when the intrinsic electrical signal was detected by each of the plurality of electrodes with a known physical location of each of the plurality of electrodes to approximate the origin of the intrinsic electrical signal further comprises comparing the vector with the timing information and location information of each of the plurality of electrodes to approximate the origin of the intrinsic electrical signal.

32. The method of claim 26, further comprising the step of determining an appropriate electrical stimulation therapy based upon the origin of the intrinsic electrical signal indicative of the atrial tachycardia.

33. The method of claim 32, further comprising the step of delivering the appropriate electrical stimulation therapy when it is determined that the intrinsic electrical signal represents an atrial arrhythmia condition.

34. The method of claim 33, wherein the therapeutic electrical stimulation is an anti-tachycardia pacing pulse train that originates at a selected electrode selected as a result of the selected electrode's relative proximity to the location of the source of the intrinsic electrical signal indicative of atrial tachycardia.

* * * * *